United States Patent [19]

Castelli

[11] Patent Number: 4,809,700
[45] Date of Patent: Mar. 7, 1989

[54] ARMLET DEVICE WITH AN ELECTRODE FOR PICKING UP PHYSIOLOGICAL ELECTRICAL POTENTIALS

[75] Inventor: Arrigo Castelli, Belvedere, Italy

[73] Assignee: Elettronica Trentina S.p.A., Cavareno, Italy

[21] Appl. No.: 24,996

[22] Filed: Mar. 12, 1987

[30] Foreign Application Priority Data

Mar. 21, 1986 [IT] Italy ................................ 53165B/86

[51] Int. Cl.⁴ .............................................. A61B 5/04
[52] U.S. Cl. ................................................... 128/644
[58] Field of Search .................... 128/639–641, 128/644, 690, 798, 802, 803, 791–793

[56] References Cited

U.S. PATENT DOCUMENTS

| 763,657 | 6/1904 | Brown | 128/802 X |
|---|---|---|---|
| 990,158 | 4/1911 | Moses | 128/802 X |
| 2,815,749 | 12/1957 | Friedman | 128/644 |
| 3,386,445 | 6/1968 | McDonald | 128/798 |
| 3,677,268 | 7/1972 | Reeves | 128/803 |
| 3,967,628 | 7/1976 | Vredenbregt | 128/802 |

FOREIGN PATENT DOCUMENTS 274612 7/1951 Switzerland ................. 128/644

Primary Examiner—Lee S. Cohen
Attorney, Agent, or Firm—Albert L. Jeffers; Richard L. Robinson

[57] ABSTRACT

An armlet device with an electrode for picking up physiological electrical potentials is described.

The electrode comprises, on one side, a pad which can come into contact, via a conductive paste, with the body of a patient, and on the opposite side, a contact stud connectable with a terminal connector of an electrical connection cable leading to apparatus for processing the said physiological potentials. The pad and the contact stud are supported by a body which is provided with tongues for connection to the armlet in such a way that the outer contact surfaces of the pad and the stud face towards opposite faces of the armlet.

8 Claims, 2 Drawing Sheets

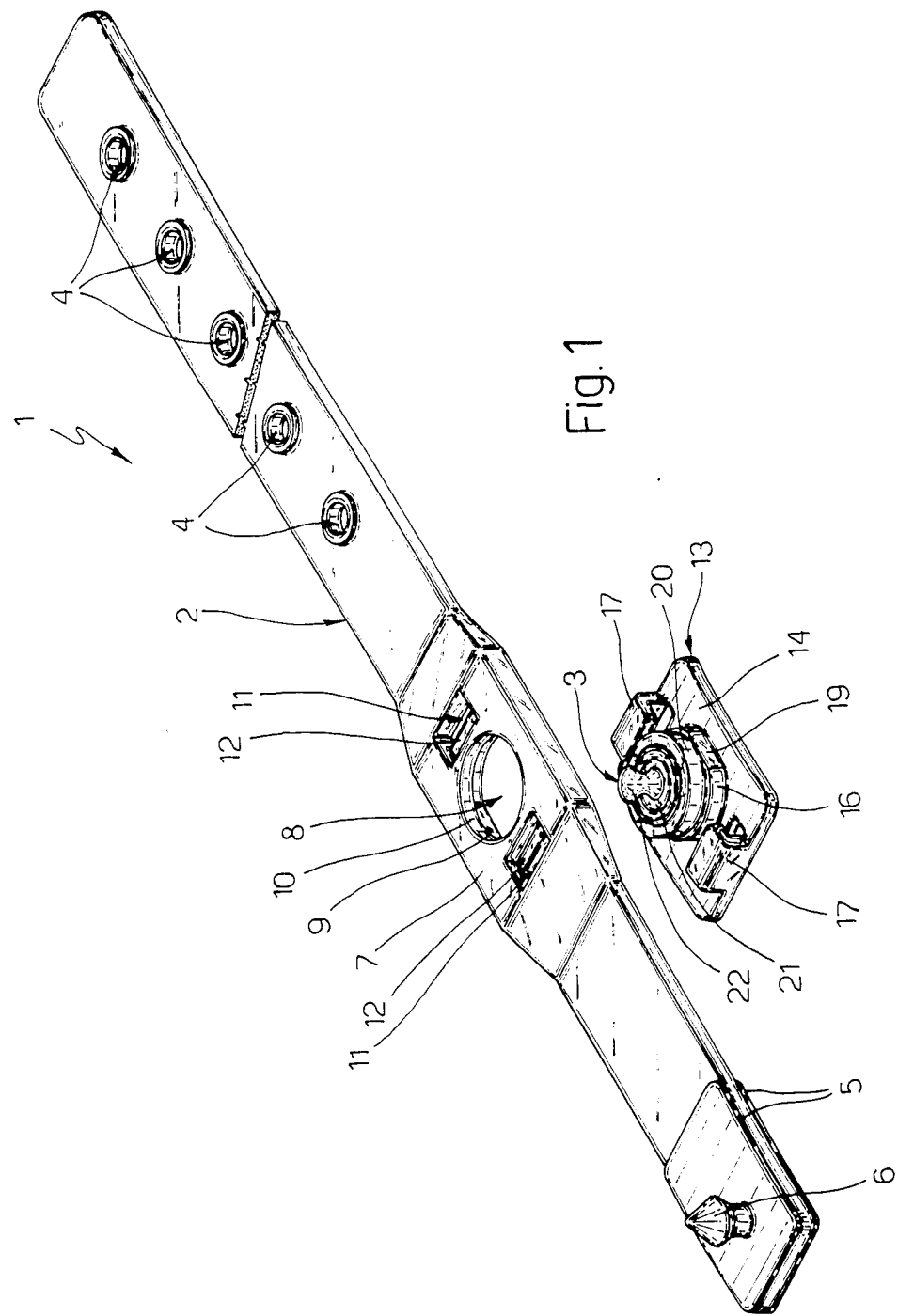

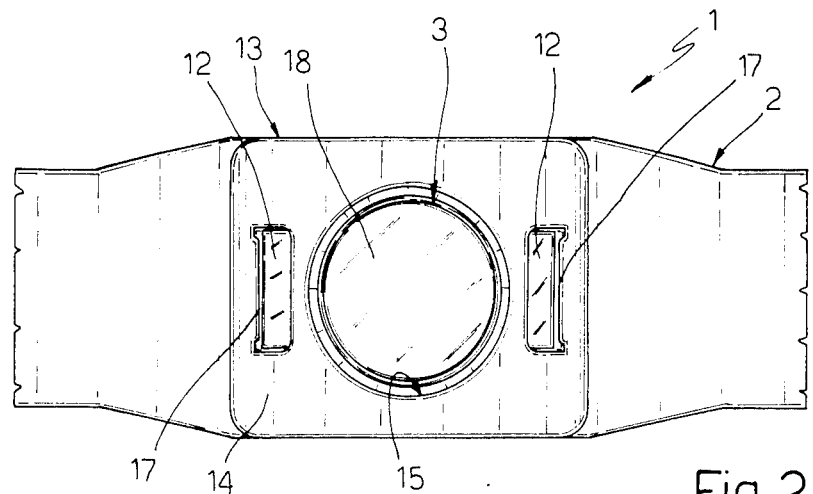
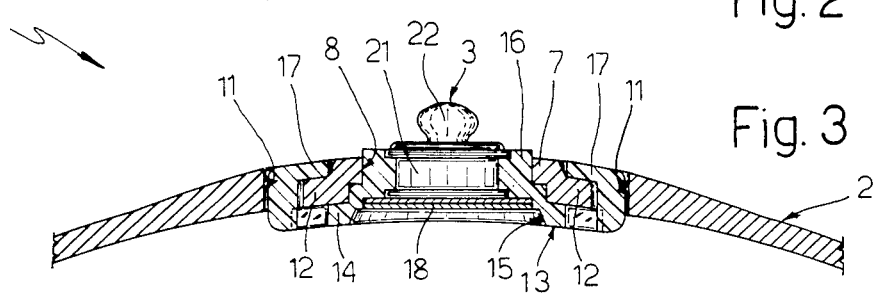
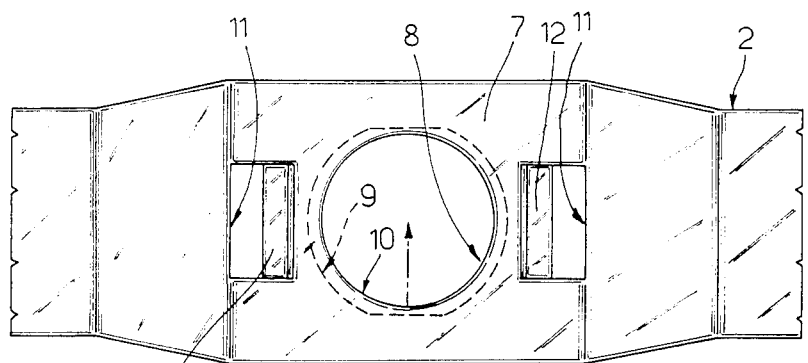
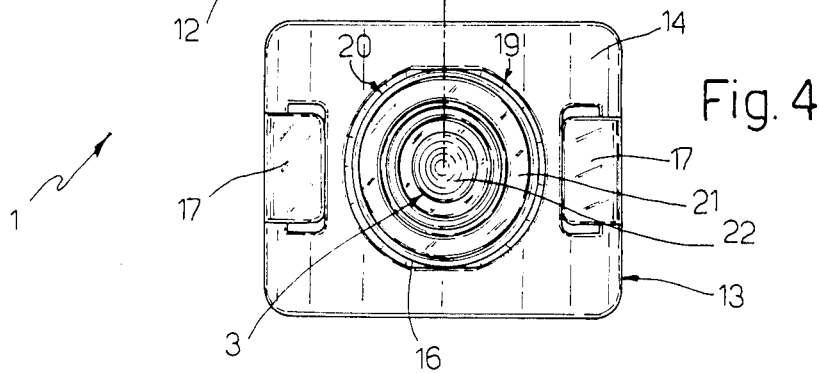

ARMLET DEVICE WITH AN ELECTRODE FOR PICKING UP PHYSIOLOGICAL ELECTRICAL POTENTIALS

BACKGROUND OF THE INVENTION

The present invention relates to an armlet device with an electrode for picking up physiological electrical potentials.

As is known, currently commercially available devices of the above indicated type essentially comprise an electrode which has a conductive pad which can come into contact, via a conductive paste, with a part of the body of a patient, a plug connection for connecting it to processing apparatus such as, for example, an electrocardiograph, and a stud attachment to the armlet.

The devices described above have various disadvantages.

In particular, the electrode thus formed is bulky and needs intermediate connectors for connecting it to the apparatus in that this latter is in general provided with stud connectors which are not adapted to fit the plug formed in the electrode.

SUMMARY OF THE INVENTION

The object of the present invention is that of providing an armlet device with an electrode for picking up physiological electrical potentials, which allows the disadvantages presented by the above listed devices of the known type to be overcome.

According to the present invention there is provided an armlet device with an electrode for picking up physiological electrical potentials, characterised by the fact that the said electrode comprises a lower pad which can come into electrical contact with a part of the body of the patient, and an upper contact stud engageable with a corresponding connector of an electrical connection cable leading to a suitable processing apparatus; the said pad and the said contact stud being supported by a body provided with means for coupling to the said armlet and partially housed in a through hole in this latter in such a way that the opposite outer contact surfaces of the said pad and the said stud are disposed in correspondence with opposite faces of the said armlet.

BRIEF DESCRIPTION OF THE DRAWINGS

For a better understanding of the present invention a preferred embodiment is now described, purely by way of non-limitative example, and with reference to the attached drawings, in which:

FIG. 1 is an exploded perspective view of a device formed according to the principles of the present invention;

FIG. 2 is a partial view, on an enlarged scale, of the device of FIG. 1 seen upwardly from below;

FIG. 3 is a section of the device of FIG. 2; and,

FIG. 4 is an exploded plan view of the device of FIG. 2.

DETAILED DESCRIPTION OF THE INVENTION

As illustrated in FIG. 1, a device, generally indicated with the reference numeral 1, comprises an armlet 2 which supports an electrode 3. The device 1 is utilised for picking up physiological electrical potentials and for this the electrode 3 is, in use, connected to apparatus, not illustrated, such as for example, an electrocardiograph.

The armlet 2 is preferably made of elastically deformable material and has a section in which is formed a plurality of through holes 4 distributed uniformly along the longitudinal axis of this section. One end of the armlet 2 is enclosed between two plates 5 made of plastics material of rigid type and having a slight curvature in the longitudinal direction of the armlet 2. Upwardly from the upper plate 5 extends a stud 6 which, in use, is engaged in one of the holes 4 to allow the armlet 2 to be closed, for example, around a limb of a patient. The armlet 2 further has an intermediate portion 7 of greater thickness and width than the adjacent portions of the armlet itself. In the portion 7 is formed a circular through hole 8 having a lower section 9 and an upper section 10 of different diameter (FIGS. 1 and 4). The lower section 9 is of greater diameter and has two diametrically opposite facing surfaces subtended by respective chords parallel to the longitudinal direction of the armlet 2.

At the opposite sides of the hole 8 there are formed two essentially rectangular slots 11 passing through the portion 7, each of which slot has two sections, respectively, a lower and an upper section, of different widths which define an inner shoulder 12. The lower section is that of reduced width.

With reference to FIGS. 1, 3 and 4 the electrode 3 is encapsulated in a body 13 of plastics material of rigid type, which is connected to the portion 7 of the armlet 2. The body 13 includes a substantially rectangular base plate 14 and has a central through hole 15 from the upper edge of which a tubular projection 16 extends upwardly, this tubular projection having two sections, a lower section 19 and an upper section 20, of different inner and outer diameter. In particular, the lower section 19 of the projection 16 has a reduced height and is that of greater inner and outer diameter. This lower section 19 has two diametrically opposite outer zones, the surfaces of which are delimited by respective parallel planes for the purpose of engaging the lower section 9 of the hole 8 shaped in a complementary manner (FIGS. 1 and 4). On the other hand the upper section 20 of the projection 16 engages the upper section 10 of the hole 8.

Close to the opposite lateral edges of the plate 14 there are upwardly extending associated tongues 17 in the shape of an inverted L, each of which engages one of the rectangular slots 11 in the armlet 1. The engagement of the tongue 17 in the slot 11 is achieved by pressing the tongue 17 upwardly in such a way that a bent upper portion of this hooks onto the shoulder 12 mentioned above.

As illustrated in FIGS. 1, 3 and 4, the electrode 3 comprises a pad 18 made of upper and lower conductive layers, respectively made of silver chloride and silver. The pad 18 is situated in correspondence with the lower section of the projection 16. The electrode 3 further includes a central cylindrical portion 21 which rigidly engages the upper section of the element 16. Upwardly from the upper face of the portion 21 extends a contact stud 22 which, in use, engages the corresponding connector of an electrical connection cable leading to the said apparatus.

The assembly of the body 13 with the electrode 3 onto the portion 7 of the armlet 2 is easy to effect in that it is sufficient to make the projection 16 enter into the hole 8 and the tongue 17 to enter the slots 11 exploiting the elastic deformability of the armlet 2 using as light pressure. In use, a conductive paste is spread on the part of the body of the patient from which it is desired to pick up the electrical potentials. Then the armlet 2 is fixed, taking care to position the portion 7 and therefore the pad 18 of the electrode 3 in correspondence with this conductive paste, likewise ensuring that this latter is disposed within the hole 15 of the plate 14 in such a way as to obtain electrical contact with the pad 18.

From what has been described the advantages which can be achieved using the present invention will be evident.

In particular, the electrode 3, however it is formed, does not require the use of intermediate connectors for connecting with the apparatus, in that the stud 22 allows a direct electrical connection thereof to the connector carried by the electrical connection cable of the apparatus. In fact, the types of apparatus currently in commercial use have the terminal of their electrical cables shaped in such a way as to be engaged by a stud of the same type as the stud 22. The electrode 3 has a reduced bulk; finally, the body 13 is simple to make and easy to assemble on the portion 7 of the armlet 2.

Finally, it is clear that the device 1 described above can be modified and varied without by this departing from the scope of the present invention.

I claim:

1. An armlet device with an electrode for picking up physiological electrical potentials, comprising:
    an armlet having opposite faces, a through hole, and a pair of through slots disposed to either side of said through hole;
    an electrode including an electrically conductive lower pad which can come into electrical contact with a part of the body of a patient, and an electrically conductive upper contact stud engageable in a corresponding connector of an electrical connection cable of suitable processing apparatus, said pad and said stud having outer opposite contact surfaces; and
    a body supporting said pad and said contact stud, said body including a base plate, said body partially housed in said through hole of said armlet in such a way that the outer opposite contact surfaces of said pad and said stud are disposed in correpsondence with said opposite faces of said armlet, said body provided with connection means for connection to said armlet, said connection means including two tongues extending from said base plate of said body which engage respectively said pair of through slots of said armlet.

2. A device according to claim 1 in which said tongues are of inverted L-shape and have an upper bent portion, and said slots have lower and upper sections of different width defining an inner shoulder, said upper section being that of greater width and housing said upper bent portion of said tongue, said upper bent portion engaging said shoulder.

3. A device according to claim 1 in which said body includes a tubular portion having an upper part and a lower part, said electrode includes a central portion which rigidly engages said upper part, said pad engages said lower part, and said contact stud extends upwardly from said central portion.

4. A device according to claim 3 in which said base plate includes a central zone having a through hole having an upper edge, said tubular portion extending upwardly from said upper edge of said through hole of said central zone; said through hole of said central zone defining with the outer contact surface of said pad, a cavity able to receive a conductive paste which establishes, in use, an electrical connection between said pad and the body of said patient.

5. A device according to claim 1 in which said through hole in said armlet is situated in correspondence with an end portion of said armlet, said end portion being provided with a stud engageable, in use, with a respective auxiliary hole forming one of a plurality of through holes in said armlet on an end portion opposite that carrying said stud to allow fixing of said armlet to said part of the body.

6. A device according to claim 1 in which said through hole in said armlet is situated in an intermediate portion of said armlet having a thickness and a width conveniently greater than the adjacent portions of the armlet.

7. A device according to claim 1 in which said armelt is made of a material of elastically deformable type, and said body is made of plastics material of rigid type.

8. An armlet device with an electrode for picking up physiological electrical potentials, comprising:
    an armlet having opposite faces and a through hole;
    an electrode including an electrically conductive lower pad which can come into electrical contact with a part of the body of a patient, and an electrically conductive upper contact stud engageable in a corresponding connector of an electrical connection cable of suitable processing apparatus, said pad and said stud having outer opposite contact surfaces, said contact stud extending upwardly from said lower pad; and
    a body supporting said pad and said contact stud, said body provided with connection means for connection to said armlet, said body parially housed in aid through hole of said armlet in such a way that the outer opposite contact surfaces of said pad and said stud are disposed in correspondence with said opposite faces of said armlet, said body including a tubular portion having an upper part and a lower part, said lower part and said upper part of said tubular portion being of different external and internal diameter, wherein said lower part is of greater inner and outer diameter, said through hole of said armlet having two parts, respectively a lower part and an upper part of different diameter to house said lower part and upper part respectively of said tubular portion;
    said electrode including a central portion which rigidly engages said upper part of said tubular portion, said pad engaging said lower part of said tubular portion.

* * * * *

UNITED STATES PATENT AND TRADEMARK OFFICE
CERTIFICATE OF CORRECTION

PATENT NO. : 4,809,700

DATED : March 7, 1989

INVENTOR(S) : Arrigo Castelli

It is certified that error appears in the above-identified patent and that said Letters Patent is hereby corrected as shown below:

```
Col. 3, line 1, change "as light" to --a slight--;
Claim 7, Col. 4, line 26, change "armelt" to --armlet--;
Claim 8, Col. 4, line 43, change "aid" to --said--.
```

Signed and Sealed this

Twenty-sixth Day of September, 1989

Attest:

DONALD J. QUIGG

Attesting Officer

Commissioner of Patents and Trademarks